US008384017B2

(12) United States Patent
Botto

(10) Patent No.: US 8,384,017 B2
(45) Date of Patent: Feb. 26, 2013

(54) SUBSURFACE NUCLEAR MEASUREMENT SYSTEMS, METHODS AND APPARATUS

(75) Inventor: Tancredi Botto, Cambridge, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 760 days.

(21) Appl. No.: 12/536,845

(22) Filed: Aug. 6, 2009

(65) Prior Publication Data

US 2011/0035151 A1    Feb. 10, 2011

(51) Int. Cl.
*G01V 5/00* (2006.01)

(52) U.S. Cl. ....................................................... 250/266

(58) Field of Classification Search ............. 250/390.11, 250/366, 266, 269.3
See application file for complete search history.

(56) References Cited

U.S. PATENT DOCUMENTS

| 3,047,720 | A | * | 7/1962 | Rickard | 376/153 |
| 3,202,822 | A | * | 8/1965 | Kehler | 250/266 |
| 3,772,513 | A | * | 11/1973 | Hall et al. | 376/165 |
| 4,504,438 | A | | 3/1985 | Levy et al. | |
| 5,680,423 | A | | 10/1997 | Perkins et al. | |
| 7,488,934 | B2 | | 2/2009 | Bryman | |
| 2007/0057194 | A1 | * | 3/2007 | Ryan et al. | 250/390.11 |
| 2009/0101824 | A1 | | 4/2009 | Beken | |
| 2009/0289190 | A1 | * | 11/2009 | Laine et al. | 250/370.11 |

OTHER PUBLICATIONS

Alvarez L.W., "Search for hidden chambers in the pyramids", Science vol. 167, pp. 832-839, 1970.

Alfaro, R et al, "A muon detector to be installed at the Pyramid of the Sun", Revista Mexicana De Fisica 49 Suplemento 4, pp. 54-59, 2003.
Nagamine, K. et al., "Method of probing inner-structure of geophysical substance with the horizontal cosmic-ray muons and possible application to volcanic eruption prediction", Nuclear Inst and Methods in Physics Research, pp. 585-595, 1995.
Tanaka, H et al., "Development of a two-fold segmented detection system for near horizontally cosmic-ray muons to probe the internal structure of a volcano", Nuclear Instr and Methods in Physics Research pp. 657-669, 2003.
Examination Report of Canadian Application Serial No. 2,712,121 dated Jan. 31, 2012.

* cited by examiner

*Primary Examiner* — Constantine Hannaher
(74) *Attorney, Agent, or Firm* — Jakub M. Michna; Rachel E. Greene; Brigid M. Laffey

(57) ABSTRACT

Methods and related systems are described for use for making subterranean nuclear measurements. The system can include a plurality of elongated scintillator members each generating optical signals in response to ionizing radiation. Optical detector units can be optically coupled to at least one end of each elongated scintillator member so as to detect optical signals from each elongated scintillator member. The system can be suitable for permanent or semi-permanent deployment downhole. For example, the system can operate for more than six months in a subterranean deployment measuring cosmic radiation. The system can be suited to monitor density changes in subterranean regions of interest, for example, density changes brought about by steam injection as part of a steam assisted gravity drainage operation.

31 Claims, 11 Drawing Sheets

(A-A')

(A-A')

(B-B')

SUBSURFACE NUCLEAR MEASUREMENT SYSTEMS, METHODS AND APPARATUS

BACKGROUND OF THE SUBJECT MATTER DISCLOSED

1. Field of the Subject Matter Disclosed

The subject matter disclosed relates to nuclear measurements made in a subsurface environment. More particularly, this patent specification relates to systems and methods for track determination of ionizing radiation for density measurements and/or permanent and/or semi-permanent density monitoring in a borehole.

2. Background of the Subject Matter Disclosed

Nuclear density measurements rely on the attenuation of a radiation field of known intensity traversing a region of interest. Such a transmission measurement technique requires the determination of the radiation field intensity before and after the region of interest. In a down-hole environment density measurements are typically performed in a single cylindrical bore-hole tool. This constraint typically prevents transmission type measurements.

In typical down-hole gamma-gamma density measurements, the bore-hole tool contains both one or more photon detectors and a gamma radiation source of known intensity. The formation density of interest is probed when photons emitted from the radiation source exit the bore-hole region and scatter off the formation back into the bore-hole again where they are detected by the density tool. In the energy range of practical down-hole gamma radiation sources, the above photon flux is very sensitive to a variety of environmental effects at the interface between the borehole, the tool and the formation, which affect the measured apparent formation density and must be corrected for.

Typical down-hole photon detectors used in gamma-gamma density measurements consist of a bulk of scintillating material in a suitable package and optically coupled to a photo-multiplier tube: this arrangement measures the energy deposited in the detector by an incoming photon or gamma ray but does not determine the trajectory with which the photon entered the detection volume.

Another type of density measurements uses so-called natural cosmic ray radiation, consisting of charged particles (muons) up to very high energies. Cosmic ray muons can penetrate up to several km into the subsurface and are thus of interest for subsurface density measurements probing formation densities at much larger distance scales than with gamma-gamma density and up to several tens of meters or more. However given the modest cosmic muon rate (only a few events per square inch per minute at surface, e.g., a surface of the earth, and dropping exponentially with depth) it becomes quickly unpractical to perform a muon transmission measurement over long ranges as the usable flux will be quickly significantly reduced by the practical solid angle coverage available when two detectors are placed over long distances.

SUMMARY OF THE SUBJECT MATTER DISCLOSED

According to the subject matter disclosed, at least one embodiment includes a system for making subterranean nuclear measurements. The method comprises of a plurality of elongated scintillator members each generating optical signals in response to ionizing radiation. A first optical detector unit optically coupled to a first end of each elongated scintillator member of the plurality of elongated scintillator members so as to detect optical signals from each elongated scintillator member. Finally, the method includes a housing adapted to house the plurality of elongated scintillator members and the first optical detector and being suitable for subterranean deployment.

According to aspects of the subject matter disclosed, the method may further comprise of a second optical detector unit optically coupled to a second end of each elongated scintillator member of the plurality of elongated scintillator members. Along with a processing system adapted and programmed to calculate position information for ionizing radiation based at least in part on a comparison of optical signal arrival times at the first and second optical detector units. It is possible the processing system can further be adapted and programmed to calculate trajectory information for ionizing radiation based at least in part on the calculated position information from at least two scintillator members. It is noted that the plurality of elongated scintillator members can form a bundle having an arrangement selected from one or more of the type in the group consisting of one of: a bundle of mostly collinear fibers; a bundle of fibers in a direction mostly transverse to the main longitudinal axis of the housing; a bundle of helically wound fibers; a bundle wherein one or more fibers overlap; a bundle wherein one or more fibers cross at given angles; a bundle with a rounded or polygonal cross section or some combination thereof.

According to aspects of the subject matter disclosed, each elongated scintillator member of the plurality of elongated scintillator members can be of one or more type selected from the group consisting of one of a plastic scintillator fiber, an inorganic crystal fiber, a liquid-based scintillator in a long aspect ratio geometry, a composite fiber or some combination thereof. Further, each elongated scintillator member of the plurality of elongated scintillator members can be of one or more type selected from the group consisting of one of a plurality of fibers with a rounded cross-section, a plurality of fibers with a polygonal cross-section, a plurality of fibers with a varying cross-section or some combination thereof. Further still, each elongated scintillator member of the plurality of elongated scintillator members can be of one or more type selected from the group consisting of one of: a plurality of fibers with a hollow core; a plurality of photonic-crystal fibers; microstructured fibers or some combination thereof. It is noted that at least one elongated scintillator member of the plurality of elongated scintillator members can be doped so as to enhance the elongated scintillator member's detection efficiency for one or more type of particle selected from the group consisting of one of slow neutrons, fast neutrons, gamma-rays, charged particles or some combination thereof. It is possible at least one elongated scintillator member of the plurality of elongated scintillator members can be one of doped so as enhance its optical properties or can be doped so as to better match the optical signals to the sensitivity of the optical detector unit.

According to aspects of the subject matter disclosed, the plurality of elongated scintillator members can be arranged around a hollow core volume which contains detector bias and data memory. It is possible that wherein the plurality of elongated scintillator members can be arranged around a hollow core volume through which a fluid flow channel is positioned. Further, the plurality of elongated scintillator members can be arranged around a hollow core volume which contains a Cerenkov or a transition radiation detector adapted to tag incoming ultra-relativistic cosmic ray muons. Further still, the first optical detector unit includes one or more optical detector with one or more independent optical amplification channel and each elongated scintillator member of the plurality of elongated scintillator members can be optically coupled with a different optical amplification channel. Also, the one or more optical detector can be a solid-state optical detector. Further, the one or more optical detector can be of a type selected from the group consisting of one of a photo-diode or a solid-state photo-multiplier, such that the one or more optical detector can be an electron avalanche optical detector. Further, the one or more optical detector can be of a type selected from the group consisting of one of photo-multipliers, multi-channel plates or some combination thereof. It is noted that the ionizing radiation includes gamma-rays, cosmic-ray muons, slow, fast neutrons or some combination thereof.

According to aspects of the subject matter disclosed, the method may further comprise a data storage system housed within the housing adapted to store data generated by the first detector unit. The method may also further comprise a battery system housed within the housing and adapted to supply power to the first detector unit for at least six months of operation. The method may further comprise a cable link from the surface adapted to supply power to the first detector unit for at least six months of operation. It is noted that the method may further comprise a radionuclide gamma ray nuclear source or a gamma ray electronic generator housed within the housing, and wherein the ionizing radiation can be primarily gamma ray radiation backscattered by a subterranean formation and originating from the source.

According to the subject matter disclosed, at least one embodiment includes a method for making subterranean nuclear measurements. The method comprises deploying a tool housing into a subterranean formation, the housing containing a plurality of elongated scintillator members each generating optical signals in response to ionizing radiation. Further, the method includes detecting optical signals from one or more elongated scintillator member of the plurality of elongated scintillator members using a first optical detector unit that is optically coupled to a first end of each elongated scintillator member.

According to aspects of the subject matter disclosed, the method may further comprise detecting optical signals from one or more elongated scintillator member of the plurality of elongated scintillator members using a second optical detector unit that is optically coupled to a second end of each elongated scintillator member. Along with calculating position information for ionizing radiation based at least in part on a comparison of optical signal arrival times at the first and second optical detector units. The method may also comprise calculating trajectory information for ionizing radiation based at least in part on the calculated position information and on information relating to which of the plurality of scintillator members generates optical signals. It is noted the method can comprise monitoring density changes in an underground formation based at least in part on monitoring ionizing radiation in the form of cosmic-rays traversing one or more regions of interest. Wherein the density changes can be brought about by the injection, movement or displacement of fluids caused at least in part by injection of fluid from one or more injection wells. It is noted the injection of fluid can be primarily for a purpose selected from the group consisting of one of a storage of the injected fluid in an underground reservoir, stimulation of a reservoir by injection of water, or stimulation of a reservoir by injections of gases. Further, the injection of fluid can be a steam as part of a steam assisted gravity drainage operation. It is possible the housing can further contain a battery system housed within the housing and adapted to supply power to the first detector unit for at least six months of operation. Further still, the housing may further contain a data storage system adapted to store data generated by the first detector unit. The housing also may further contain a radionuclide gamma ray nuclear source or a gamma ray electronic generator, the ionizing radiation can be primarily gamma ray radiation, and the method can further comprise measuring back-scattered gamma rays by detecting the optical signals. It is possible the back-scattered gamma rays can be measured at different distances and/or angles so as to minimize, separate and/or correct for bore-hole density effects.

According to the subject matter disclosed, at least one embodiment includes a long-term subterranean nuclear monitoring system. The system comprises a housing suitable for subterranean deployment for at least six months and a nuclear detection unit housed in the housing. The method further includes a power supply system adapted to supply power to the detection unit for at least six months of operation.

According to aspects of the subject matter disclosed, the power supply system can include a battery system housed within the housing. Further, the power supply system can include a cable link between a surface of the earth and the housing that is adapted to supply power to the detection unit. Further, the method may further comprise a data storage system housed within the housing adapted to store data from the nuclear detection unit. Further still, the method may comprise a communication system adapted to provide communication between a surface of the earth and the housing which includes one or more antennae for wireless communication. It is noted, the method may further comprise of a communication system adapted to provide communication between a surface of the earth and the housing which can include a cable between the housing and the surface. Further, the nuclear detection unit may comprise of a plurality of elongated scintillator members each generating optical signals in response to ionizing radiation. Along with a first optical detector unit optically coupled to a first end of each elongated scintillator member of the plurality of elongated scintillator members so as to detect optical signals from each elongated scintillator member. As well as a second optical detector unit optically coupled to a second end of each elongated scintillator member of the plurality of elongated scintillator members. Finally, a processing system adapted and programmed to calculate position information for ionizing radiation based at least in part on a comparison of optical signal arrival times at the first and second optical detector units.

According to aspects of the subject matter disclosed, the processing system can further be adapted and programmed to calculate trajectory information for ionizing radiation based at least in part on the calculated position information and on information relating to which of the plurality of scintillator members generates optical signals. It is noted the first and second optical detector units can consist of one or more solid-state based detector or one or more electron avalanche based detector, such that each solid-state based detector or each avalanche based detector can include at least one or more independent optical channel. Further, the method may further comprise a processing system housed within the housing and adapted and programmed to compress data collected downhole so as to reduce data storage and/or data transmission needs.

According to the subject matter disclosed, at least one embodiment includes a method for long term subterranean nuclear monitoring. The method comprising deploying a tool housing into a subterranean formation, the housing containing a nuclear detection unit, along with measuring nuclear radiation over a time period of at least six months.

According to aspects of the subject matter disclosed, the tool housing can further contain a battery system adapted to supply power to the nuclear detection unit for at least six months of operation. Further, the tool housing can also further contain a data storage system adapted to store data from the nuclear detection unit. The method may further comprise of communicating with the nuclear detection unit via a cable connection. It is noted that the method may also further comprise communicating with the nuclear detection unit via a wireless connection. Further, the nuclear detection unit may contain a plurality of elongated scintillator members, such that each generating optical signals are in response to ionizing radiation. Further still, the method can further comprise detecting optical signals from one or more of the elongated scintillator member of the plurality of elongated scintillator members using a first optical detector unit that is optically coupled to a first end of each elongated scintillator member. Along with detecting optical signals from one or more of the elongated scintillator member of the plurality of elongated scintillator members using a second optical detector unit that is optically coupled to a second end of each elongated scintillator member. Finally, the method includes calculating position information for ionizing radiation based at least in part on a comparison of optical signal arrival times at the first and second optical detector units.

According to the subject matter disclosed, the method may further comprise calculating trajectory information for ionizing radiation based at least in part on the calculated position information and on information relating to which of the plurality of elongated scintillator members generates optical signals. The method may also further comprise monitoring density changes along certain directions in an underground formation based at least in part on the measured muon radiation along the directions. It is noted the nuclear detection unit monitors muon radiation along directions that traverse a region of interest of changing density and along directions traversing a region of non-changing density outside the region of interest. Further, the density changes can be brought about by the injection, movement or displacement of fluids caused at least in part by injection of fluid from one or more injection wells. Further still, the injection of fluid can be a steam as part of a steam assisted gravity drainage operation. The method may also further comprise cementing or other permanent installation of the tool housing into position as part of the deployment. It is noted that the method may further comprise compressing data collected downhole so as to reduce data storage and/or data transmission needs.

Further features and advantages of the subject matter disclosed will become more readily apparent from the following detailed description when taken in conjunction with the accompanying drawings.

BRIEF DESCRIPTION OF THE DRAWINGS

The subject matter disclosed is further described in the detailed description which follows, in reference to the noted plurality of drawings by way of non-limiting examples of exemplary embodiments of the subject matter disclosed, in which like reference numerals represent similar parts throughout the several views of the drawings, and wherein.

DETAILED DESCRIPTION OF THE SUBJECT MATTER DISCLOSED

Figure 1:
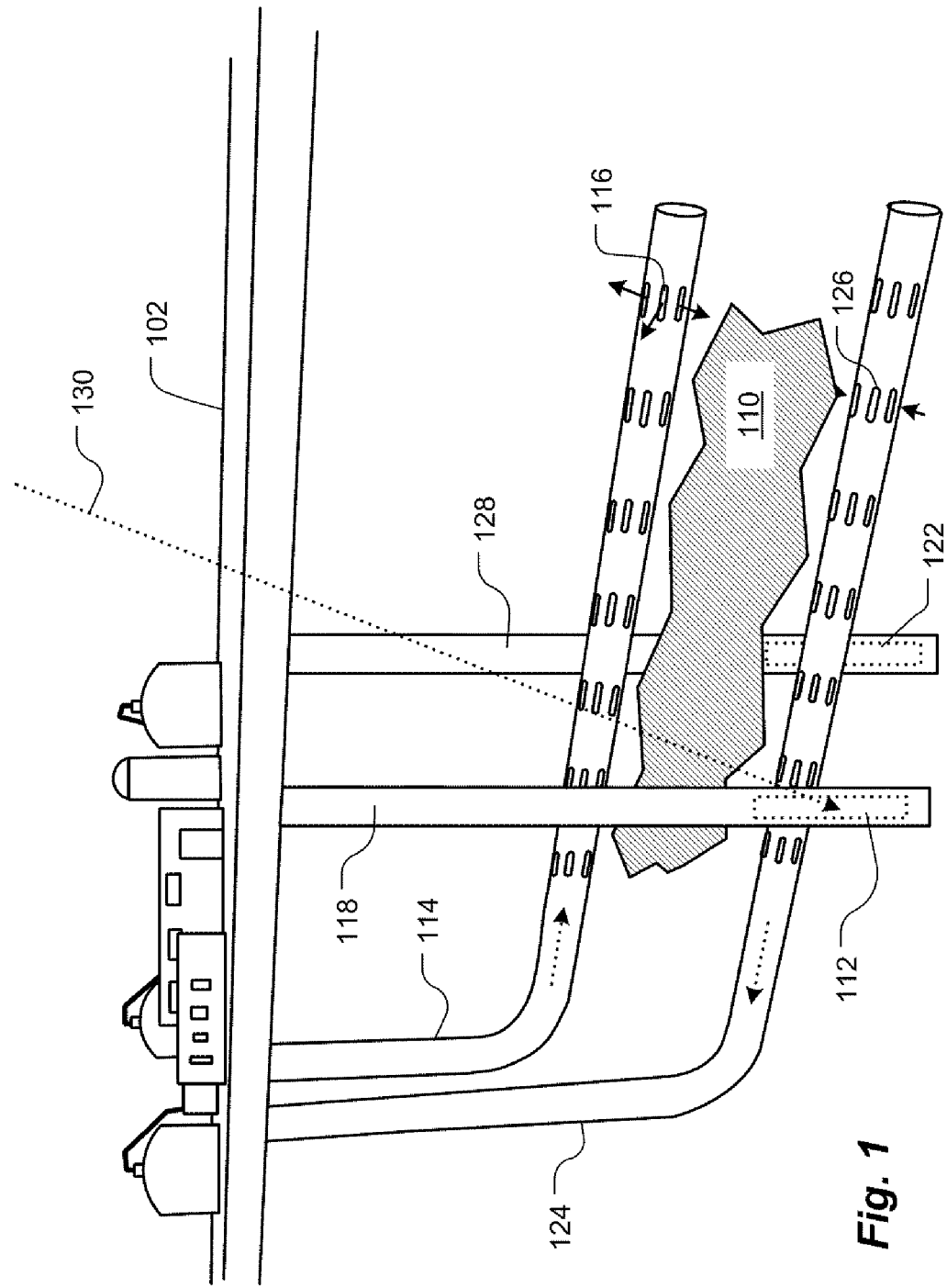
FIG. 1 shows a nuclear detector system deployed in a tar sands extraction process, according to some embodiments.

In the following detailed description of the embodiments, reference is made to accompanying drawings, which form a part hereof, and within which are shown by way of illustration specific embodiments by which the subject matter disclosed may be practiced. It is to be understood that other embodiments may be utilized and structural changes may be made without departing from the scope of the subject matter disclosed. The particulars shown herein are by way of example and for purposes of illustrative discussion of the embodiments of subject matter disclosed and are presented in the cause of providing what is believed to be the most useful and readily understood description of the principles and conceptual aspects of the subject matter disclosed. In this regard, no attempt is made to show structural details of the subject matter disclosed in more detail than is necessary for the fundamental understanding of the subject matter disclosed, the description taken with the drawings making apparent to those skilled in the art how the several forms of the subject matter disclosed may be embodied in practice. Further, like reference numbers and designations in the various drawings indicated like elements.

The spectrum of energetic cosmic rays on the earth surface is dominated by muons that are formed at the edge of the atmosphere by incoming primary cosmic radiation. The earth muon flux exhibits a peak at energies of around a few GeV (1-10, depending on angle) followed by a long tail up to much higher energies (>>10 TeV), wherein the flux drops rapidly with energy (~$1/E^{3.7}$). Even at energies as high as 1 TeV, the earth surface flux is of approximately 10000 events per square meter per day. Such high-energy particles can penetrate layers of rock up to 1 km.

Ultimately the penetrating muons are slowed down and stopped due to energy loss. Muon energy loss in the subsurface follows the well-known mechanisms common to all charged particles, namely radiative and ionization losses predicted by the Bethe-Block formula. This implies that for a given underground layer thickness (density×length) one can accurately determine the minimum entrant muon energy required to penetrate it. Conversely, knowing the distribution of cosmic muons entering a region (a "formation") of unknown thickness or density, a measurement of the muon flux at depth directly yields the integral of density×length along the muon trajectory through the formation.

Since the incoming cosmic ray flux at surface can be measured or obtained through simulations (or a combination of both) and by simple geometry the subsurface path-length of a cosmic ray event measured with a down-hole track-sensitive detector can be determined, these facts can be exploited to obtain a measurement of the average subsurface density along any direction with which cosmic ray have traversed a formation. The relative sensitivity of the density measurement will be inversely proportional to the spacing between detectors, however the absolute accuracy is only a question of statistical accuracy, and thus of measurement time.

The incoming muon flux at the earth surface varies due primarily to latitude, the earth magnetic field, the density of the air column traversed and because of "space weather" conditions (e.g. solar storms and solar wind patterns). The average rate at depth is well known and has been confirmed by many underground or underwater experiments. The total rate at a depth of ~1200 m in standard rock ($\rho$=2.65 gr/cm$^3$, Z=11, A=22) or, equivalently, at a depth of ~3000 m in sea-water, is equal to approximately 10 events per hour, per square-meter. Given their high energies, muons at moderate depths are essentially traveling along straight lines, with minimal multiple scattering introduced by underground formations. This means that the muon flux is directional, a feature that can be utilized to map of their subsurface propagation trajectories, and therefore the subsurface density (subsurface tomography).

The muon flux above or below surface can be measured in a variety of ways (such as with scintillators, gaseous, solid-state and Cerenkov detectors). Below surface, the detectors can fit in a borehole tool or station location at a given depth. Surface detectors measuring the incoming flux may be of simpler planar geometry. Muon detectors will generally be sensitive also to background radiation (such as K, Th, U, in the subsurface). However this is typically low in energy and can be effectively shielded from without affecting the measurement of multi-GeV muons. Compared to typical borehole logging conditions, the temperature requirements on the detectors may be less stringent given the moderate depths where muon density measurements are typically practical.

FIG. 1 shows a nuclear detector system deployed in a tar sands extraction process, according to some embodiments. The heavy oil in region of interest 110 is being extracted using a steam assisted gravity drainage (SAGD) process. Lower well 124 is drilled laterally along the bottom of region 110 and upper well 114 is drilled laterally about five meters above region 110. Steam is injected with the upper well 114 to vents such as vents 116. The heat mobilizes the bitumen, which allows it to flow into the lower well 124 through openings such as openings 126. Nuclear detector units 112 and 122 are deployed in separate wells 118 and 128 respectively. Muon track 130 is shown passing from the surface 102, through region 110 and detector 112. According to embodiments, the detector units 112 and 122 are permanently or semi-permanently deployed and are used to monitor the density of region 110 over time.

Figure 2:
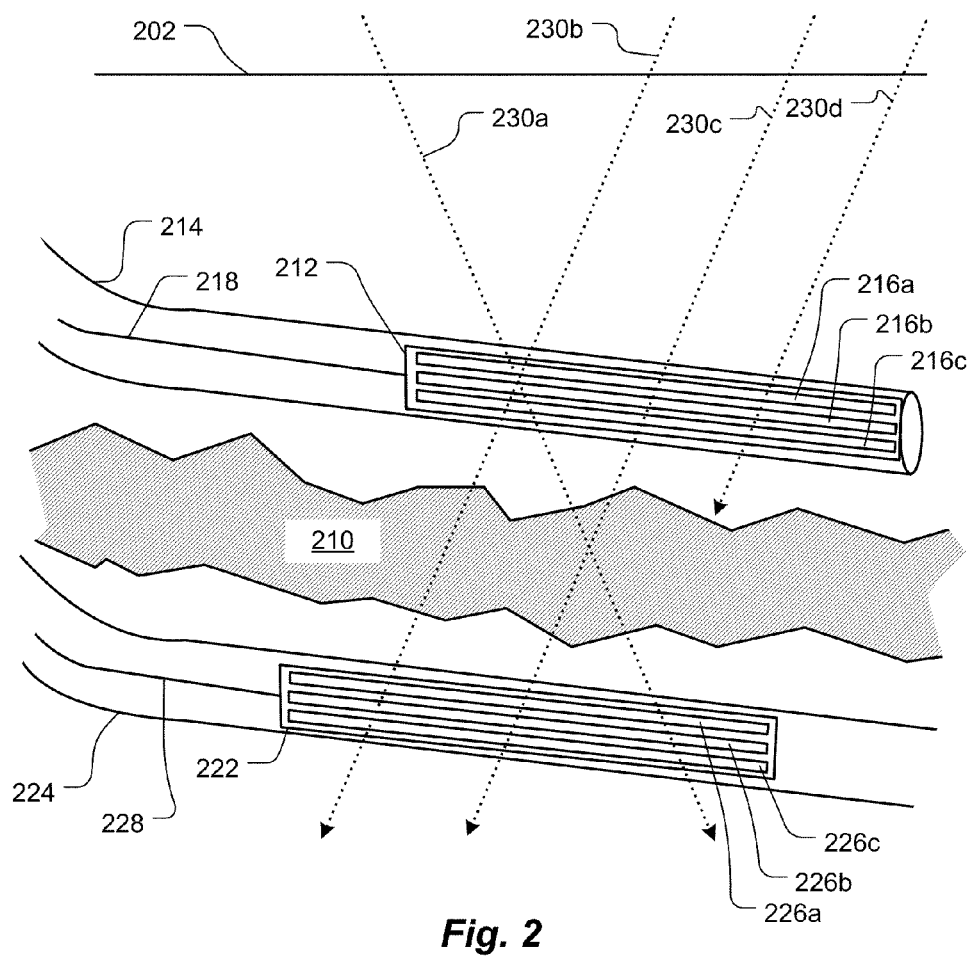
FIG. 2 shows a dual nuclear detector system including one subsurface bottom detector unit below a given region of interest.

FIG. 2 shows a dual nuclear detector system including one subsurface bottom detector unit below a given region of interest, coupled to a top detector unit above the region, according to some embodiments. Two sets of borehole tools (top detector unit 212 in borehole 214 and bottom detector unit 222 in borehole 224) measure the subsurface muon flux traversing a region of interest 210 below the surface or sea floor 202. Detector units 212 and 222 may optionally be powered and/or interrogated using cables 218 and 228 respectively. Alternatively, the detector units can be equipped with battery and data storage as is described in further detail herein. The relative count rate of unit 222 vs unit 212 is determined primarily by the properties of the formation in the intermediate region of interest 210. By utilizing a variety of position-sensitive segmented detectors such as detectors 216a, 216b and 216c in unit 212, and detectors 226a, 226b and 226c in unit 222, one can reconstruct the muon tracks. For example, as shown in FIG. 2, muon tracks 230a, 230b, 230c and 230d are detected by top detector unit 212 while only muon tracks 230a, 230b and 230c are detected by bottom detector unit 222. Utilizing standard techniques one can then invert the data to reconstruct a 3-dimensional density map of the region of interest 210. By choosing the proper relative detector alignment and measuring events simultaneously crossing both detectors, muon events that traversed the region of interest can be tagged. The relative rate of bottom detector unit 222 vs. top detector unit 212 will be dependent primarily on the properties of the intermediate region between the two detector units, averaged along the muon track, and is essentially independent on the absolute normalization of the incoming muon flux at a specific time or geographical location.

Figure 3:
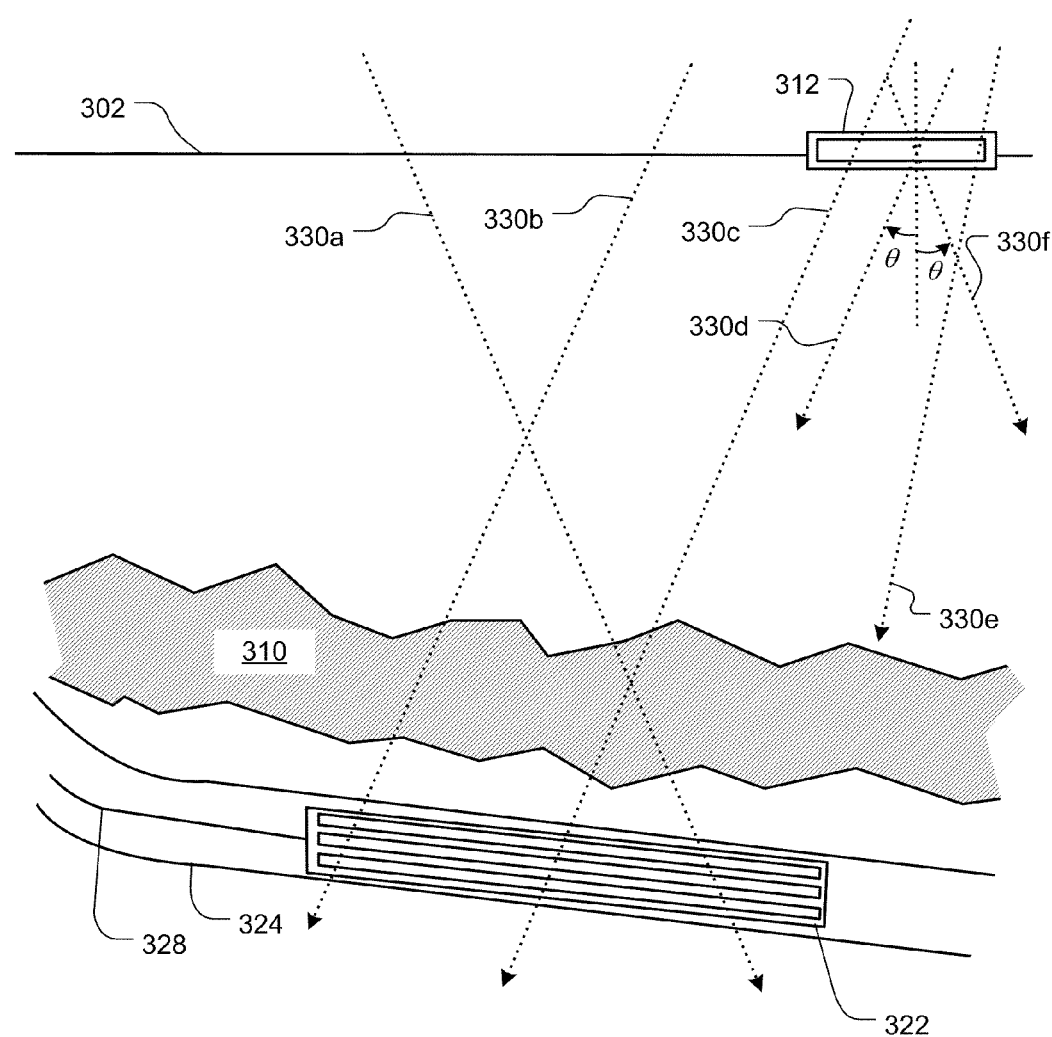
FIG. 3 shows a dual nuclear detector system including one subsurface bottom detector unit below a given region of interest, and a top detector unit on or close to the surface, according to some embodiments.

FIG. 3 shows a dual nuclear detector system including one subsurface bottom detector unit below a given region of interest, and a top detector unit on or close to the surface or sea floor, according to some embodiments. The top detector unit 312 is at or close to the surface 302 and acts as an independent monitor with which to normalize the flux measured in a down-hole detector unit 322 in borehole 324 to the total incoming muon flux. Detector unit 322 may optionally be powered and/or interrogated using cable 328. Alternatively, the detector unit 322 can be equipped with battery and/or data storage as is described in further detail herein. In FIG. 3 the down-hole count rate depends on the properties of the whole subsurface layer traversed by the muons, which may be larger than the region of interest. For example, muon tracks 330a and 330b and 330c are detected by down-hole detectors unit 322 while tracks 330c, 330d and 330e are detected by top detector unit 312. However, the relative frequency of either type of events can be described by one common flux distribution function, either measured or simulated. For example, muons such as muon track 330f, having an incoming angle $\theta$ with respect to the true vertical and not on a trajectory towards region 310 can be monitored by surface monitor 312 to determine the rate of all cosmic rays having the same incoming angle with respect to vertical, including rays such as muon track 330d which has an incoming angle $\theta$ and is on a trajectory towards region 310.

Figure 4:
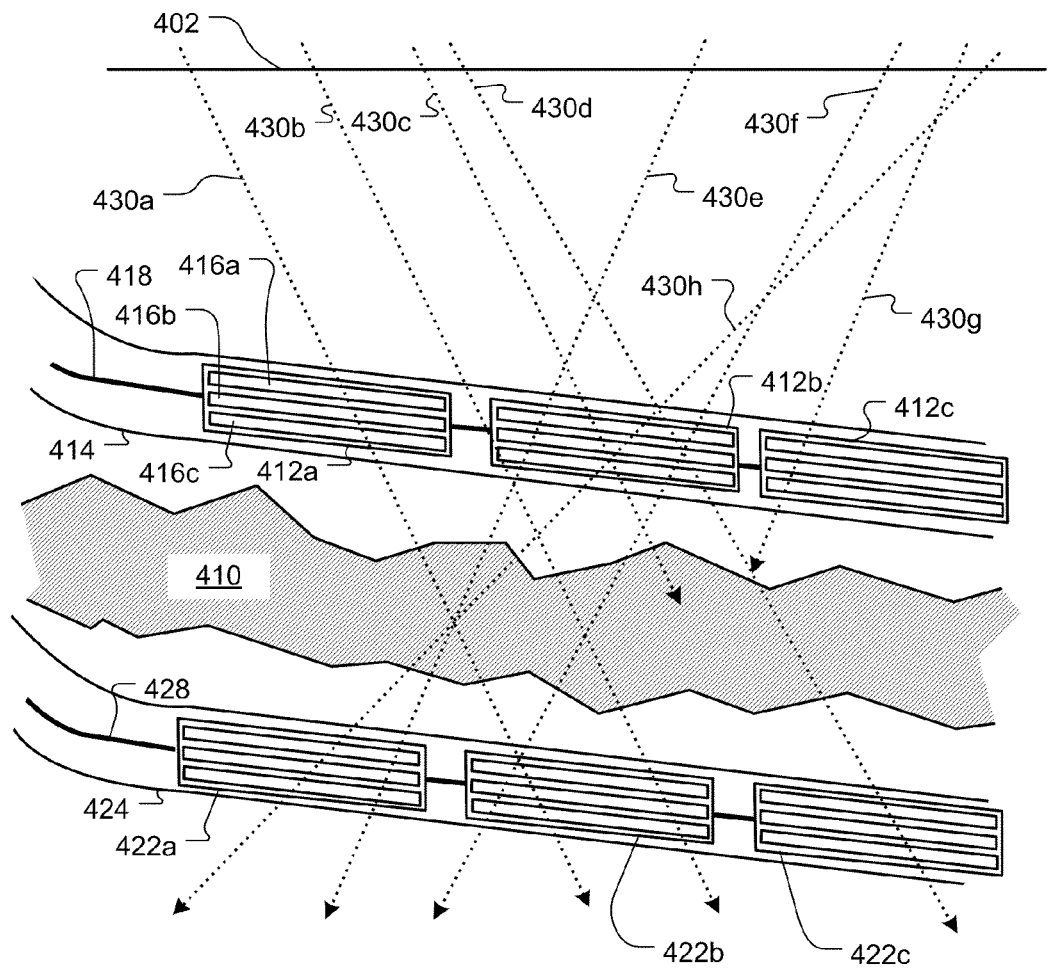
FIG. 4 shows a nuclear detector system including multiple bottom and/or top detector units, according to some embodiments.

FIG. 4 shows a nuclear detector system including multiple bottom and/or top detector units, according to some embodiments. In borehole 414 three top detector units 412a, 412b and 412c are positioned above region of interest 410 and below the surface or sea floor 402. In borehole 424 three bottom detector units 422a, 422b and 422c are positioned below region of interest 410. Detector units 412a, 412b, 412c, 422a, 422b and 422c may optionally be powered and/or interrogated using cables 418 and 428. Alternatively, the detector units can be equipped with battery and data storage as is described in further detail herein. As can be seen the different combinations of muon tracks 430a, 430b, 430c, 430d, 430e, 430f, 430g and 430h are detected each of the units. By combining the rate among pairs of detectors allows one to measure the density of the intermediate region along different directions. As a function of the relative positions of the detectors, their relative distances and the muon flux distribution, a two-dimensional subsurface density distribution can be mapped, limited by the detector active area and relative spacing, as well as the total depth and thickness of rock traversed and the related muon-flux attenuation. When the detectors are positioned such that different pairs will measure intersecting muon tracks, the region of under study can be sub-divided in voxels and a 3-dimensional reconstruction of the subsurface density distribution can be obtained with standard inversion techniques. Although only three detector units are shown in each borehole, it is understood that other numbers of detector units can be deployed depending on the application. According to some embodiments, the bottom and/or top detectors may have multiple layers to more accurately determine the muon track. For example, detector unit 412*a* is divided into three position sensitive layers 416*a*, 416*b* and 416*c*. This allows for an even finer reconstruction and an improved selection of coincident events for any of the configurations described above.

According to some embodiments, the bottom detector unit(s) are able to determine the muon tracks while the top detector unit(s) acts as an independent monitor of the local terrestrial muon flux. Instead of utilizing coincident events between two downhole detectors, the subsurface count is now normalized to the monitor rate and events that traversed the region of interest are selected in the analysis of the recorded tracks. This configuration has at least one advantage of increased statistical accuracy, coverage and operational simplicity.

According to other embodiments, other implementations are also possible. These include cross-well measurements between well pairs, for which the measurement geometry may differ from above.

As it is its energy that determines the muon penetrating power it is important to know the incoming energy distribution at all depths where the top or monitor detector is located. The so-called primary spectrum of high-energy cosmic radiation bombarding the earth is well known and understood both experimentally and theoretically. Further, several ground and sub-surface measurements of the muon flux exist. Thus the incoming muon distribution can be predicted with reasonable accuracy and, as needed, such distribution can be calibrated against measurements at varying depths through known rock thicknesses.

Figure 5:
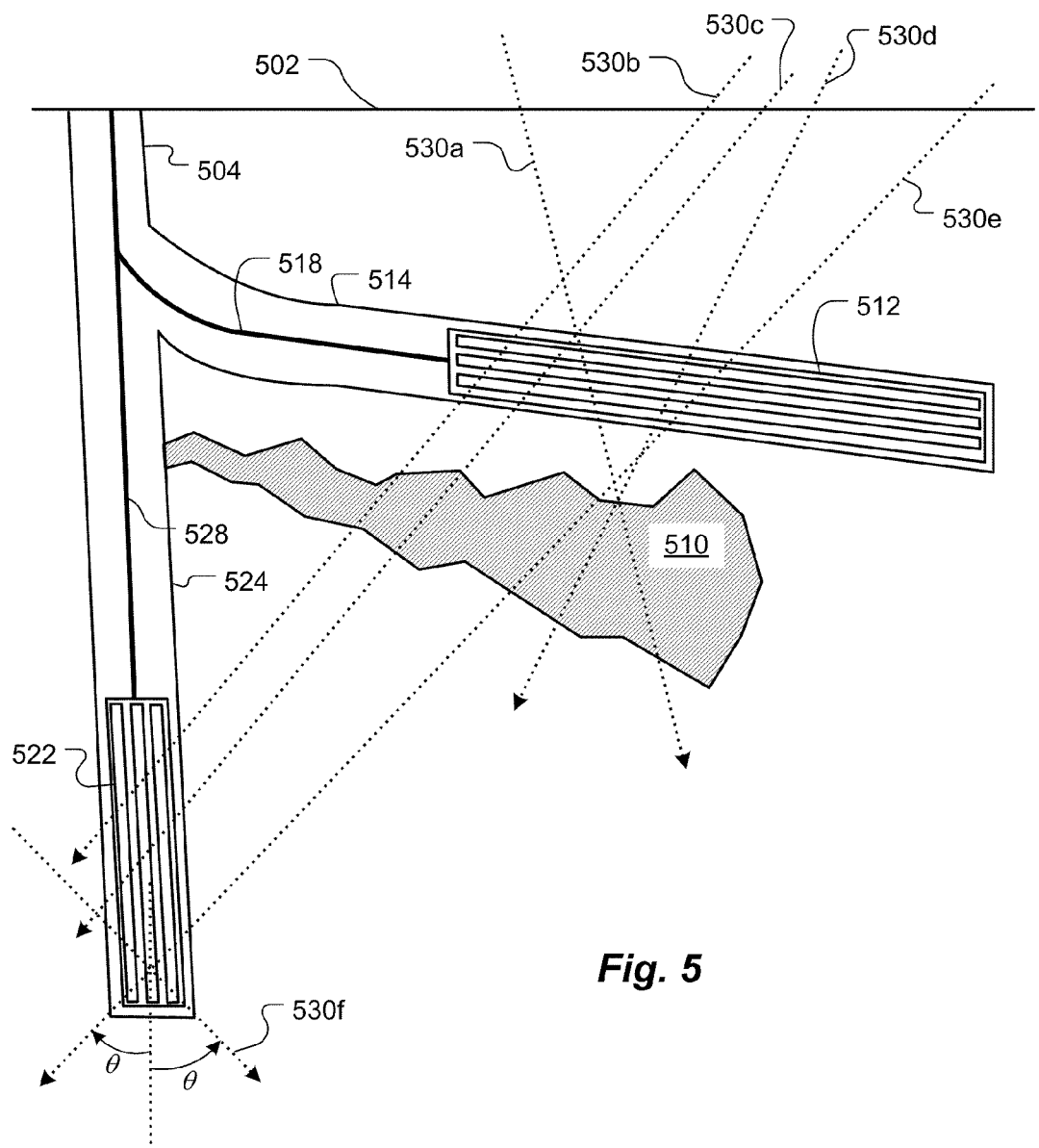
FIG. 5 shows a shows a nuclear detector system for monitoring changes of the density and/or the displacement of fluids, according to some embodiments.

FIG. 5 shows a nuclear detector system for monitoring changes of the density and/or the displacement of fluids, according to some embodiments. Changes in the density and/or displacement of fluids in the intermediate region can be determined, e.g. by two detector units 512 and 522 that are positioned in wellbores 514 and 524 respectively. Detector units 512 and 522 may optionally be powered and/or interrogated using cables 518 and 528 respectively. Alternatively, the detector units can be equipped with battery and data storage as is described in further detail herein. Note that in this case, wellbore 524 and lateral wellbore 514 both branch from a main borehole 504. Although not shown in FIG. 5, according to other embodiments, the upper detector unit 512 is located on the surface or sea floor 502. The system as shown in FIG. 5 is useful to monitor density changes that occur in reservoirs when, for instance, a fluid or gas is injected into a formation to either displace production fluids (such as hydrocarbons) or when subsurface storage of fluids is desired, such as underground storage of $CO_2$. In these cases the injection profiles give rise to underground plumes, such as plume 510 that are both complex in shape and hard to predict. As can be seen the different combinations of muon tracks 530*a*, 530*b*, 530*c*, 530*d*, 530*e*, and 530*f* are detected by at least one of the units 512 or 522. According to some embodiments, cosmic rays at a given angle can be determined by downhole detector units. For example, muons such as muon track 530*f*, having an incoming angle $\theta$ with respect to the true vertical and not on a trajectory through region 510 can be monitored by unit 522 to determine the rate of all cosmic rays having the same incoming angle with respect to vertical, including rays such as muon track 530*e* which has an incoming angle $\theta$ and is on a trajectory through region 510.

As with other nuclear density logging techniques, the accuracy of muon radiography measurements is essentially limited by the statistics of events measured at the detectors, i.e. by the number of muons measured at a given direction. However, given the high-energies involved, subsurface muon radiography measurements are independent of most borehole and tool effects. The techniques described herein can be applied to a wide variety of scenarios were large-scale density maps at moderate depths (preferably up to ~1000 m in rock) are desired, and are particularly relevant to cases for which long measurement times are acceptable. In general, reducing the spacing between detectors enhances the sensitivity to the density in the region of interest and maximizes the solid angle for coincident detection. On the other hand, increasing such spacing allows one to map out the formation density to large distances or at large angles.

Alternative measurements of subsurface density over comparable scales essentially include only cross-well and surface-based seismic measurements, and/or gravimetry. They all have poorer overall accuracy, sensitivity, and/or spatial resolution and often involve long measurement or analysis times. Surface seismic mapping in particular relies on particular features of the reservoir such as the presence of proper subsurface boundary reflectors that may not be present in unconsolidated reservoirs such as tar sand deposits.

The use of muon radiography provides by non-limiting example, advantages of much higher accuracy and much better directional information when longer measurement times can be tolerated. Also, by permanently or semi-permanently deploying the detectors, the techniques disclosed here can be used to monitor density changes over time.

In order to obtain more accurate measurements it is useful to accurately know the position of the subsurface tools and/or detectors. This can be obtained using a variety of methods currently available from the well logging industry, including making use of wireline logging positioning techniques, magnetometers, accelerometers and global positioning systems.

According to some embodiments a new class of subsurface track-sensitive nuclear detectors based on scintillator fibers is provided. According to other embodiments, by non-limiting example, a new class of density measurements that conveniently exploit the scintillator fiber unique advantages for gamma-ray, fast neutron and muon detection can be provided.

Scintillation-based detectors are ideal for many bore-hole use applications with, compared to gas detectors, high detection efficiencies for all types of incoming ionizing radiation. Scintillators do not require a gas feed system, or a HV bias system, and are typically enclosed in a ruggedized hermetic package which makes them not susceptible to pollution or contamination thus allowing for stable operation over years. While in general photo-multiplier tubes used for the optical read-out of the detector require some form of high voltage, according to some embodiments, one can also use photodiodes or Si-photomultipliers or other semiconductor based photo-detectors, which are low-voltage devices.

Scintillators can be fabricated in a variety of shapes, making them suited to miniaturization or segmentation, in order to better conform to the requirements of borehole tools. Finely segmented scintillation detectors such as scintillator fibers can for practical purposes be considered as independent sensors, and thus the loss of one channel has a minimal impact on the overall performance of the bore-hole tool. As used herein, the term "scintillator fiber" means any large aspect-ratio shapes of scintillator material, including but not limited to long strips of an optimized cross section of scintillator material. According to some embodiments, the scintillator fibers can be plastic scintillator fiber, inorganic crystal fiber, liquid-based scintillator material in a fiber shape, and/or composite fiber. In the case of a liquid-based scintillator material, the material can be sealed in a fiber shape, or according to other embodiments is free to flow in and out of a fiber-like channel.

When ionizing radiation is deposited in a scintillator, an optical signal is generated. This light will propagate in the material, undergoing multiple reflections when scattering off the inner walls. Ultimately, scintillation photons will reach the entrance of an optical detector, which converts the light into an electrical signal. This process occurs over measurable time scales of a few ns per meter of optical path-length, depending among other things on the detector properties, its geometry and on how the light is coupled to the detector itself.

In a scintillator fiber as described above, optical photons emitted from a primary ionizing event will propagate in both directions and can be collected at both ends of the fiber with a pair of optical detectors. Then, the relative difference in arrival times of the signal photons in the two detectors is a measure of the relative position of where the primary ionization events occurred along the scintillator length. The sum of the arrival times is instead a constant value, representing the total effective optical length of the scintillator.

Relative position accuracies of ~1 cm or better along the length of a scintillator fiber have been demonstrated for a variety of geometries. The particle or radiation traversal point is further constrained by the fiber finite transverse dimensions. By combining the measurements of multiple scintillating fibers or strips, such as those described, arranged in a so-called bundle one is able to reconstruct a track or direction of the incoming radiation.

Figure 6A:
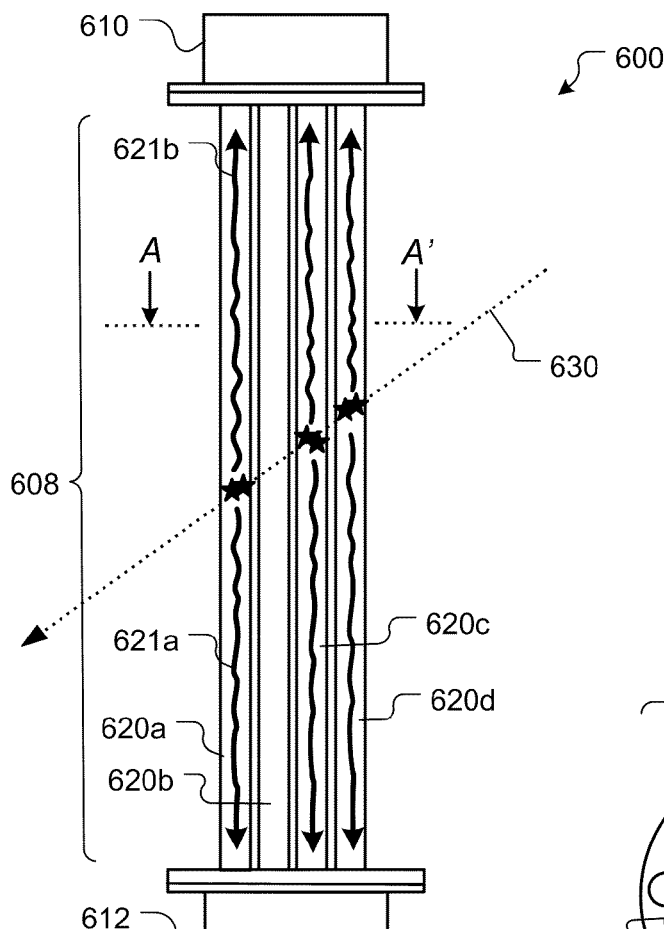
FIGS. 6a-g show sets of scintillator fibers is arranged in bundles, according to some embodiments.
Figure 6B:
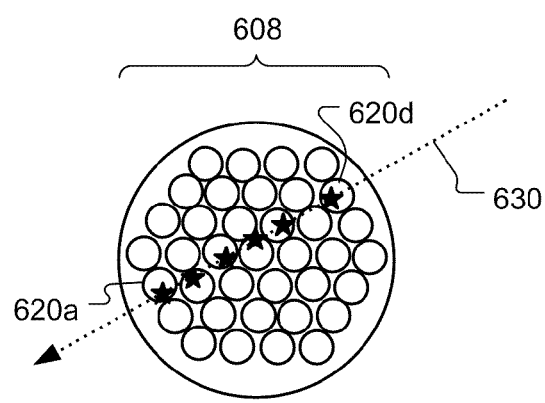
Figure 6C:
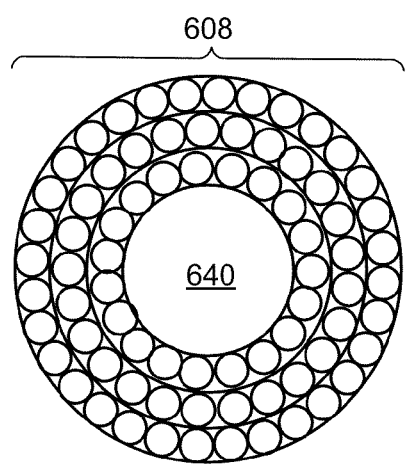

FIGS. 6a-c show a set of scintillator fibers arranged in a collinear vertical bundle, according to some embodiments. In FIG. 6a, detector unit 600 includes an upper multi-channel optical detector 610, bundle 608 and lower multi-channel optical detector 612. Bundle 608 includes a number of individual scintillator fibers such as fibers 620a, 620b, 620c and 620d. Each fiber is coupled at both the top and the bottom end to a single channel of optical detectors 610 and 612. When ionizing radiation such as that of electrons, gamma's or muons enters the scintillator bundle, for example muon track 630, it generates optical signals, such as optical signals 621a and 621b, whose travel times to each of the detector ends is dependent on the length of scintillator material traversed. The difference in top and bottom arrival times correlates with the position of the ionization event impact point along the fiber. FIG. 6b shows a cross section of the detector unit shown in FIG. 6a, according to some embodiments. As shown, muon track 630 crosses some of the individual fibers of bundle 608. The transverse position is constrained by the transverse fiber or detector dimensions. In this way, multiple impact points can be correlated to a single reconstructed track.

For each event, the signal arrival time at each detector unit can be encoded according to well known time digitization techniques. The optical detectors 610 and 612 may be any optical amplification device. According to some embodiments, a photo-tube, or a semiconductor-based photo-diode or photo-multiplier, such as Si-PMT (Si-photomultipliers), or a combination of one or more detectors each with one or more independent optical channels is used for optical detectors 610 and 612.

For a given position resolution along the fibers, the track reconstruction accuracy will generally depend on the number of fibers producing a signal, and thus on the efficiency of light conversion. Each fiber hit determines an impact point and a minimum of two points is required to determine a trajectory. With more points, a more accurate reconstruction is generally possible and/or more advanced track reconstruction and/or data processing may be used, including signal-to-noise reduction techniques. The system of multiple fibers or strips can be arranged and/or packed in a number of ways in order to optimize the detection coverage.

Thin enough fibers are generally flexible and may be arranged in a variety of shapes, including a helix-like pattern so that fibers in different layers can cross at an optimized angle with respect to each other. FIG. 6c shows an arrangement of the scintillator fibers around a hollow core, according to some embodiments. The bundle 608 surrounds hollow core 640 at the center of the borehole tool. According to some embodiments, core 640 is where the digitizing electronics are placed in order to maximize coverage along the tool axis. According to some other embodiments, core 640 is used for a fluid flow path, for example for produced fluid or an injection fluid. According to some other embodiments, core 640 may be used to host a Cerenkov detector, which can be uniquely designed to be sensitive to radiation emitted by deeply ultra-relativistic events, thus offering a convenient tag of cosmic-ray muons. According to some other embodiments, the fibers can be layered in concentric circles or semi-circles around the tool axis, including circles slightly offset from each other. According to some embodiments, the scintillator fiber diameter may be from a fraction of mm up to a few cm, for typical lengths in the range about 0.5-5 m. It is possible, 2 or more fibers can be provided. According to some embodiments each bundle 608 includes up to about 100 individual fibers.

Figure 6D:
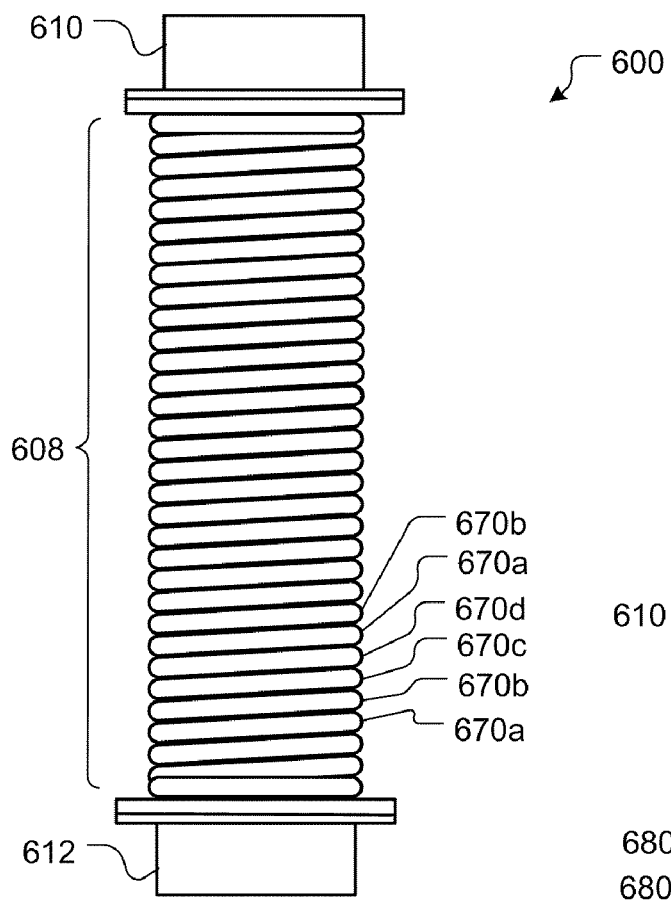
Figure 6E:
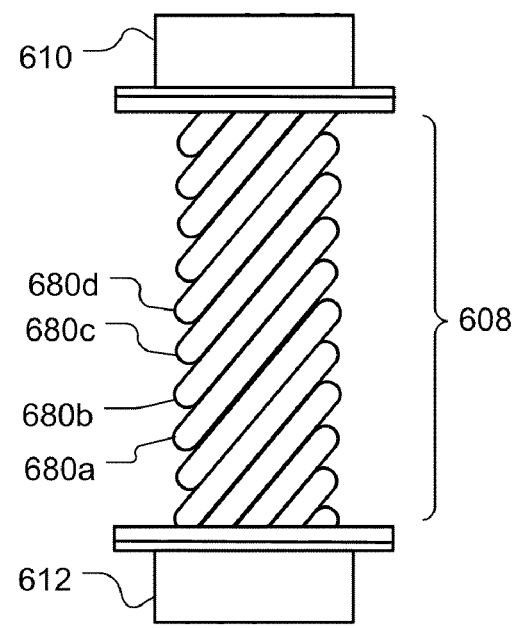

FIG. 6d shows a set of scintillator fibers arranged in a helically wound bundle, according to some embodiments. Detector unit 600 includes an upper multi-channel optical detector 610, bundle 608 and lower multi-channel optical detector 612. Bundle 608 includes a number of individual scintillator fibers such as fibers 670a, 670b, 670c and 670d. Each fiber is coupled at both the top and the bottom end to a single channel of optical detectors 610 and 612. In this example, the four fibers 670a, 670b, 670c and 670d are wound around a cylindrical core, such that fiber 670a is wound directly above 670d as shown. Note that according to some embodiments the optical detectors 610 and 612 may be oriented at any angle with respect to the tool or fiber bundle axis. Note also that detectors 610 and 612 may be replaced with a number of single channel optical detectors which may be distributed at different or multiple locations along the tool. According to some embodiments and by non-limiting example, it may be preferable for spacing, packing and/or cost reasons to introduce a flexible optical fiber coupling between one or more of the scintillator fibers and one or more of the optical detector channels. FIG. 6e shows a set of scintillator fibers arranged in another helically wound bundle according to some embodiments. The arrangement of bundle 608 includes scintillator fibers 680a, 680b, 680c and 680d in a pattern similar to that shown in FIG. 6d, although the winding of each fiber is at a smaller angle with respect to the main tool axis. According to some embodiments, combinations of helically wound fibers are provided. For example layers of fibers can be wound around a central core at different angles or in an opposite direction (e.g. in a mirror image to those shown in FIGS. 6e and 6e), so as to provide multiple layers of fibers having a cross section similar to that shown in FIG. 6c. According to yet further embodiments, one or more layers of windings as shown in FIG. 6d and/or 6e can be wound around a central core of vertically arranged fibers such as shown in FIGS. 6a and 6b.

Figure 6F:
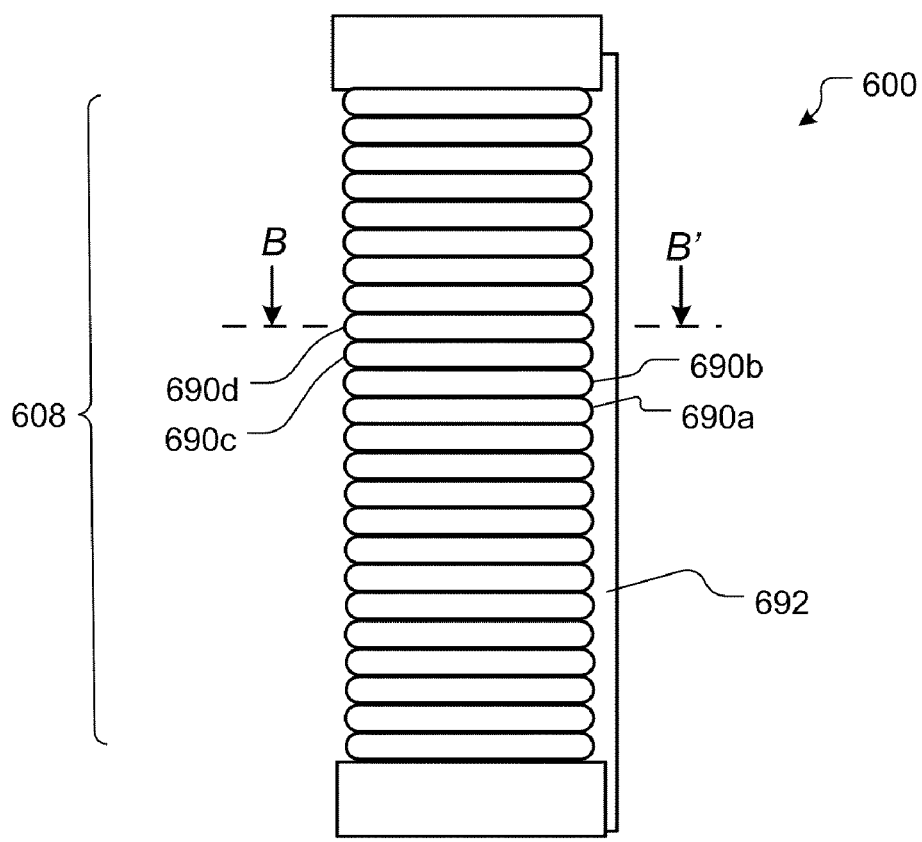
Figure 6G:
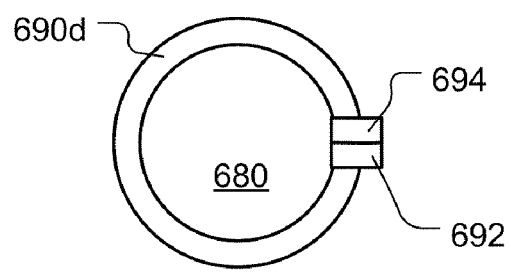

FIGS. 6f-g show a set of scintillator fibers wound in a plane primarily perpendicular to the tool axis, according to some embodiments. FIG. 6g is a cross section along B-B'. Detector unit 600 includes two multi-channel optical detectors 692 and 694 (which can be the same or similar to optical detectors 610 and 612 described above, and bundle 608. Bundle 608 includes a number of individual scintillator fibers such as fibers 690a, 690b, 690c and 690d. Each fiber is semi-circular and coupled at one end to a single channel of optical detector 692 and at the other end to optical detector 694. In this example, the four fibers 690a, 690b, 690c and 690d are wound around a cylindrical core 680.

According to yet other embodiments, the number of available fibers their position reconstruction accuracy and their individual detection efficiencies can be optimized by choosing one value or a range values for their diameter and/or size and shape, such that the combined tool detection efficiency is still large enough to provide a sufficient event rate, and the signal-to-noise and/or track reconstruction capability is optimized by having a larger number of hits. This may include bundles of fibers with unequal diameters, so as to maximize their packing density or with unequal lengths, so as to optimize the packing of the optical read-out channels.

According to yet other embodiments, including any combination of the configurations described above, some of the fibers in the system are collected together and coupled to a single multi-channel photo-detector such as a segmented phototube or Si photo-multiplier. All of the methods described herein can be used in combination with one other.

Having an optimized, track-sensitive, scintillator detection system, improved subsurface density measurements can be performed which are relevant to the E&P industry.

In the case of so called gamma-gamma density, one typically compensates for bore-hole environmental effects (such as effects due to mud-cakes, filtrates, tool stand-off, bore-hole diameter, bore-hole fluids, casing, cement) by utilizing the energy information in the back-scattered photon spectra recorded at two or more locations along the tool. The back-scattered gamma-ray event rate at the borehole generally decreases as one moves away from the gamma-ray source. At the same time, the increased distance creates a focusing effect such that the relative fraction of photons that has probed deeper into the formation increases. These latter photons carry formation density information that is generally less sensitive to environmental effects and of greater measurement value, that those photons measured closer to the source.

Typical gamma-gamma density correction schemes make use of multiple detectors at different distances from the source and sometimes in combination with appropriate focusing and/or collimation schemes at the source and/or at the detectors, such that different detectors will be primarily sensitive to a different mix of contributions from the borehole and tool background as well as contributions from the intrinsic formation signal, such as contributions from different average distances in the formation.

A track sensitive detector would allow one to selectively focus on the subset of deeper probing gamma-rays on an event-by-event basis, based on their re-entry angle at the tool, with many advantages relative to existing bore-hole gamma-gamma density measurements where this information is not available.

Track sensitive detectors such as those described herein can also be used to perform sub-surface density measurements utilizing deeply penetrating cosmic rays. For the reasons given in the background section, at least one implementation for such measurements is with a detector at depth able to identify cosmic-ray muons and distinguish those that have traversed a certain region of interest based on their incoming direction.

According to some embodiments, information from a bore-hole cosmic-ray detector is combined with that of an independent monitor detector able to determine the local cosmic-ray flux. In this way an absolute value of the average formation density in a region of interest can be inferred.

According to some embodiments, the detectors and associated techniques described herein are utilized in cosmic ray flux measurements that probe the change of formation density over time. Such changes may occur for instance when fluids are injected into a subsurface formation, including injection of steam, water, gases ($CO_2$, $N_2$), super-critical $CO_2$, and in general when fluids are injected to either displace hydrocarbons in place or for long-term storage. In this case a relative measurement of the cosmic ray flux at depth as a function of time is sufficient.

A scintillator-based muon detector as described herein can measure muon events from all directions, including those where the reservoir density does not change over time. According to some embodiments, this property provides a valuable and efficient built-in muon detection monitor for use with a cosmic-ray bore-hole tool.

A fiber-based scintillation detector, as described herein, is ideally suited for measurements described above with respect to FIGS. 1-5, also because the segmentation of the detector can be arranged so as to better match the geometry and orientation of the region of interest under investigation with respect to the geometry and orientation of the available bore-holes where the tool is to be inserted.

Figure 7:
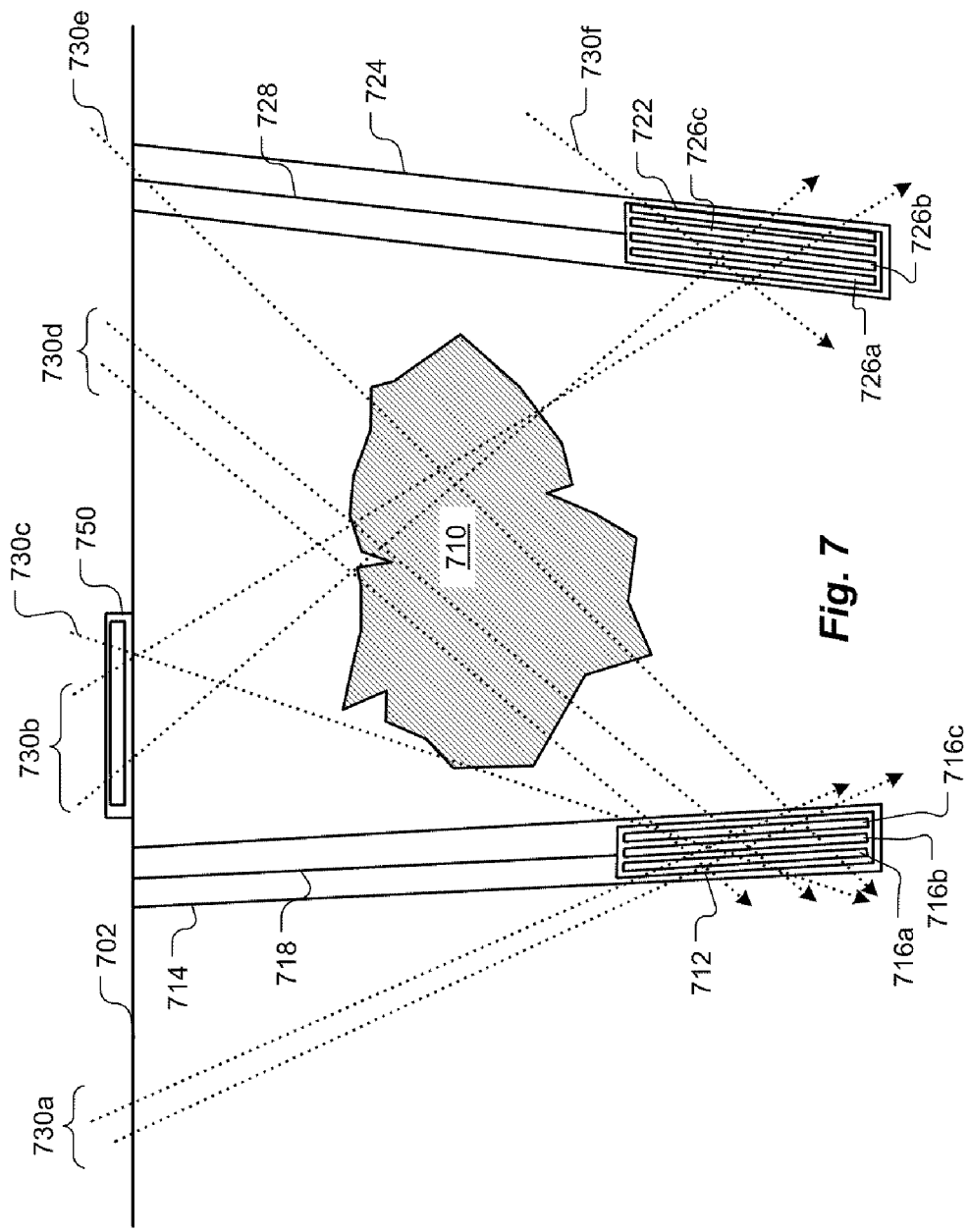
FIG. 7 shows an arrangement of nuclear detectors for subsurface monitoring, according to some embodiments.

FIG. 7 shows an arrangement of nuclear detectors for sub-surface monitoring, according to some embodiments. A surface detector 750 is at or close to the surface of sea floor 702 and acts as an independent monitor with which to normalize the flux measured in down-hole detector units 712 and 722, deployed in boreholes 714 and 724 respectively, to the total incoming muon flux. Note that although surface detector 750 is shown located above the region of interest 710, according to some embodiments, the detector 750 can be located elsewhere while still providing a measurement or monitoring of the muon flux rate for incident angles corresponding to the angles of interest-given the relative position of the region of interest 710 to the downhole detector units 712 and 722. Thus although muon tracks 730b and 730c are shown passing though surface detector 750 and also through region 710 and then one of the downhole detector units, according to some embodiments, the surface detector 750 is located on the surface some miles away from the region 710 and nevertheless is used to measure a representative muon flux over the time period of interest.

In the case shown in FIG. 7, the down-hole count rate depends on the properties of the whole subsurface layer traversed by the muons, which may be larger than the region of interest 710. Muon tracks 730a are shown passing through detector unit 712 but not though region 710. Muon tracks 730b are shown passing through surface detector 750, region 710 and detector unit 722. Muon track 730c is shown passing through surface detector 750, region 710 and detector unit 712. Muon tracks 730d and 730e are shown passing through region 710 and detector unit 712. Finally, muon track 730f is shown passing through detector 722 but not through region 710. According to some embodiments, a surface detector such as detector 750 is not relied upon to normalize the flux measured by downhole detector units 712 and 722, but rather measurements from the downhole detectors themselves are used.

For example, the muon flux, such as with muon tracks 730$a$ and 730$f$, that is measured by a downhole detector but, due to its angle, has traversed a region of stable density rather then region of interest 710, can be used as the reference incoming muon flux during measurements that monitor changes in density in region 710.

Thus, according to various embodiments, the incoming muon distribution can be simulated with reasonable accuracy using any one or a combination of three different techniques. Namely: (1) a surface detector (such as shown in FIGS. 3 and 7); (2) a downhole nuclear detector separate from the monitoring detector (such as shown in FIGS. 2, 4 and 5); and (3) the monitoring downhole detector itself (by measuring other flux arriving from angles away from the region of interest). Using any one or more of these techniques, will serve to calibrate and normalize any changes in the down-hole muon count rate due to a change in the intensity of the cosmic ray flux at the surface rather than density changes in the subterranean formations.

Additionally, down-hole detector unit 712 includes multiple scintillator detector sets such as sets 716$a$, 716$b$ and 716$c$, each of which include a bundle of individual scintillator fibers as described with respect to FIG. 6. Similarly detector unit 722 includes multiple scintillator detector sets such as sets 726$a$, 726$b$ and 726$c$. Detectors units 712 and 722 may optionally be powered and/or interrogated using cables 718 and 728 respectively. Alternatively, the detector units can be equipped with battery and data storage as is described in further detail herein.

According to some embodiments, the arrangement as described with respect to FIG. 7 is used for monitoring of time evolving plumes of injected fluids, such as $CO_2$, $H_2O$ or gases. Another example is the injection of steam in so-called heavy-oil or tar-sand reservoirs. In such embodiments, the detectors 712 and 722 are permanently or semi-permanently deployed in boreholes 714 and 728 respectively. For example, according to some embodiments, detectors 712 and 722 are cemented in place in boreholes 714 and 728 respectively.

Figure 8:
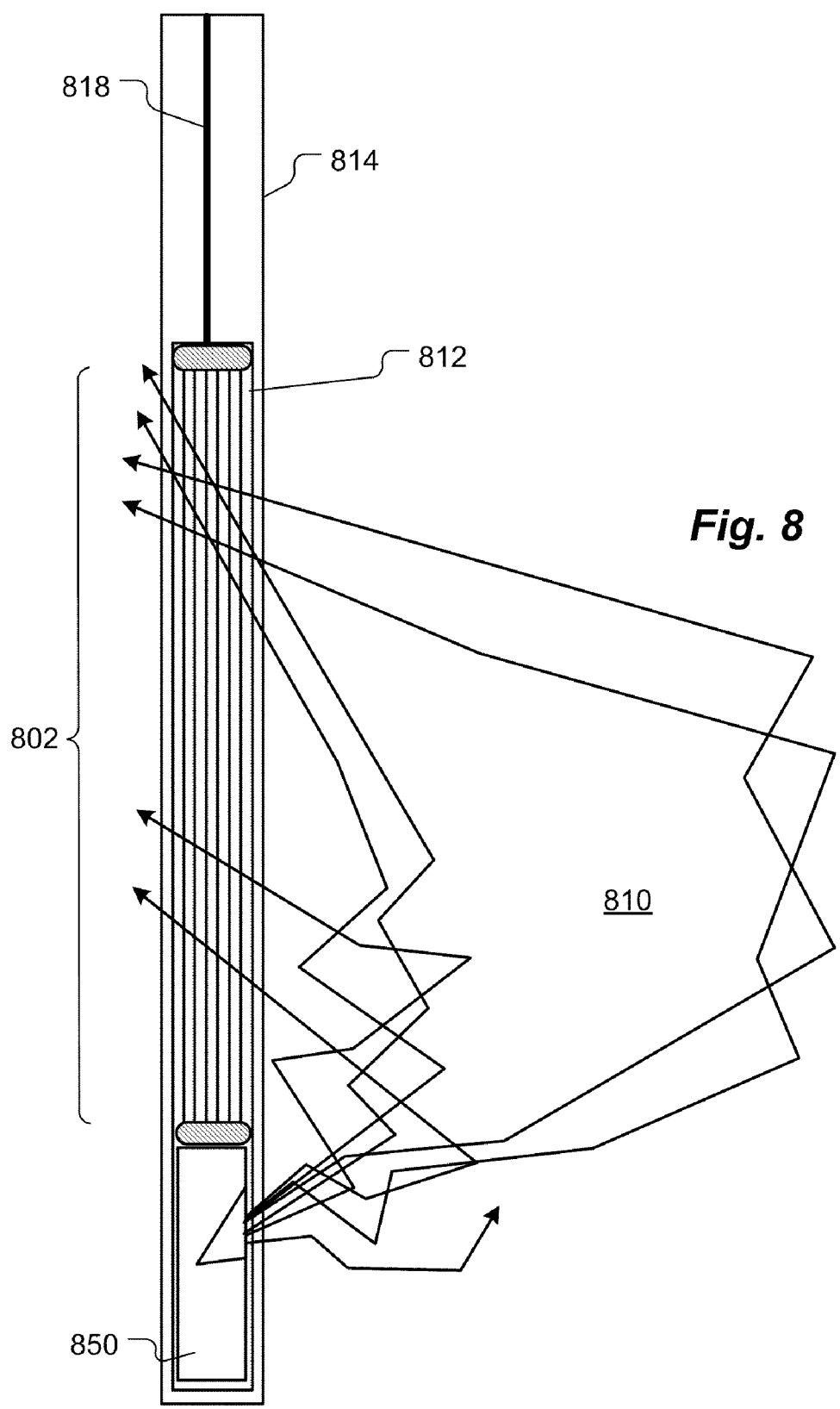
FIG. 8 shows an example of a scintillator fiber based nuclear detectors for measuring back-scattered gamma rays in a gamma-gamma density tool according to some embodiments.

FIG. 8 shows an example of a scintillator fiber based nuclear detectors for measuring back-scattered gamma rays in a gamma-gamma density tool according to some embodiments. In this case, gamma-gamma density tool 802 includes a nuclear source 850 and multiple detectors 812 for improved volume coverage and reconstruction. Detectors 812 include a plurality of scintillator fiber bundle units such as described in with respect to FIG. 6. Source 850 generates nuclear radiation which is scattered in region of interest 810 and detected by detectors 812. According to some embodiments, the scintillator fiber detectors 812 are used to make a selection, such as to focus primarily at different distances into the formation so as to minimize, separate and/or correct for bore-hole density effects.

Figure 9:
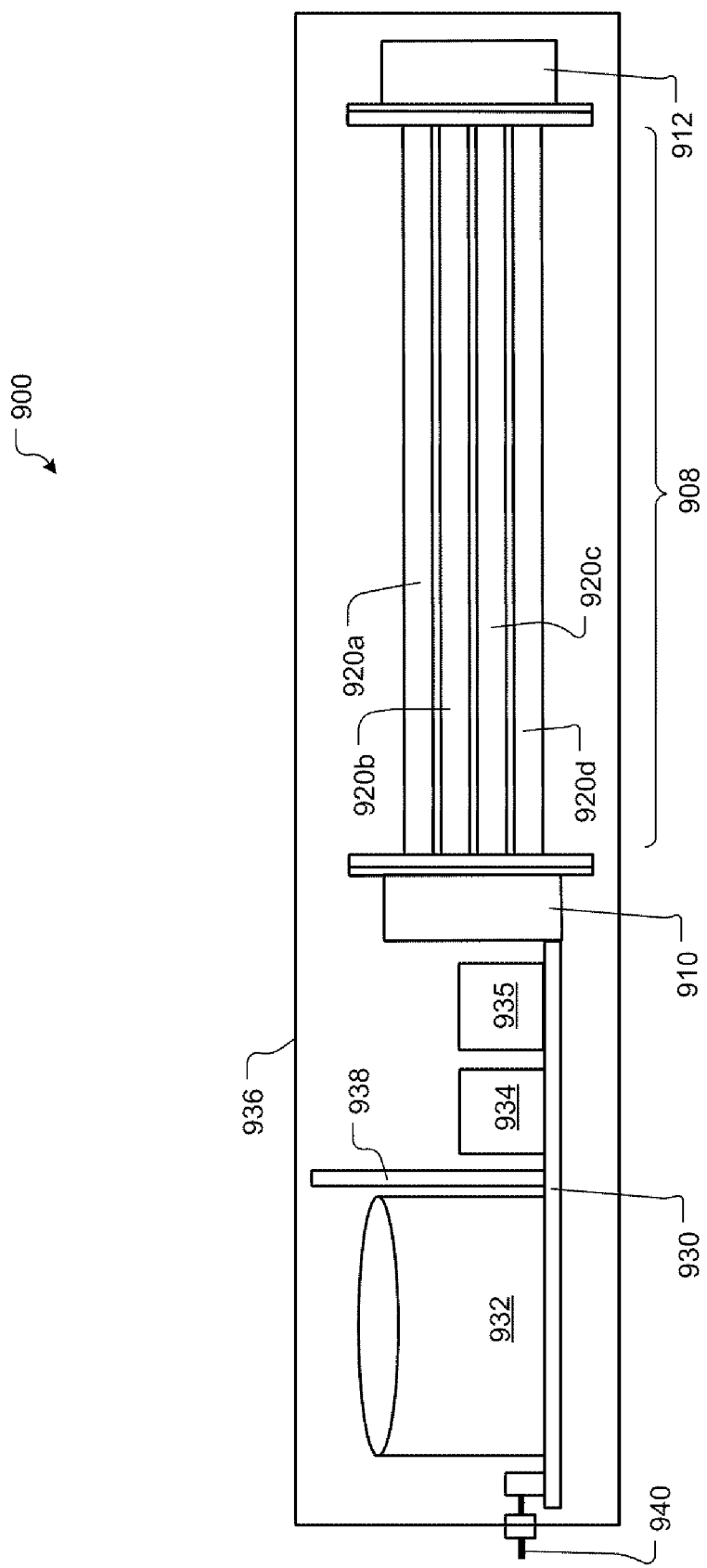
FIG. 9 shows detector assembly for permanent or semi-permanent deployment downhole, according to some embodiments.

FIG. 9 shows detector assembly for permanent or semi-permanent deployment downhole, according to some embodiments. Detector assembly 900 includes a housing 936 that houses a fiber based scintillator detector. The detector includes scintillator bundle 908 which is made up of a plurality of scintillator fibers such as fibers 920$a$, 920$b$, 920$c$ and 920$d$. Each of the fibers are optically connected on one end with a first photo detector 910 and on the other end with a second photo detector 912. The photo detectors 910 and 912 are multi-channel with each channel connected to each scintillator fiber. Alternatively, the detectors may include multiple single-channel sub units each connected to one end of a scintillator fiber, and/or any combination of the foregoing. The photo detectors 910 and 912 can be photo-diodes or solid-state photo-multipliers or avalanche photo-multipliers or micro-channel plates and/or any other optical amplification device. The detectors 910 and 912 are each connected to an electronics board 930 on which it is mounted electronics including a long term storage unit 934 such as flash based memory, and one or more processors 935. The electronics on the electronics board can also include a processor programmed to provide data compression downhole so as to alleviate the need for data storage and/or data transmission. A battery 932 supplies enough power for the electronics and photo detectors for the anticipated deployment of the assembly 900. For example, assembly 900 can be deployed downhole for more than 6 months. According to some embodiments, assembly 900 can be deployed downhole for more than 12 months. To retrieve the data stored in the assembly 900, several options are available. First, the assembly can be retrieved following the deployment. Second, an antenna 938 can be used to communicate wirelessly to an interrogating probe that is periodically positioned near the assembly during deployment. Finally, an external connection 940 can be provided for wired communication with other downhole components or with the surface. According to some embodiment, detector assemblies such as assembly 900 are used for the detectors in the embodiments shown and described herein with respect to each of the other figures.

According to other embodiments, Gaseous Electron Multiplayers (GEMs) are used as the detectors for the arrangements described with respect to FIGS. 1-5. GEMs are widely used in high-energy particle physics. They typically consist of multiple layers of patterned foils held in a gas volume. GEM foils may be bent and arranged in concentric cylindrical shapes that are ideal geometries for borehole tools. The foils contain micron-size holes with high aspect ratios, produced via chemical etching or laser ablation. By keeping two sides of a foil at a moderate potential difference a very high electric field can be generated in the hole-region due to its inherent aspect ratio. Primary charge liberated in the gas by the ionizing track of a cosmic ray, will drift into the hole-region where is accelerated and generates secondary charge. This amplification process is very robust and yields gains in excess of 1000 per layer, for a potential difference of a few 100 Volts. Multiple layers can be stacked to further increase the gain. The bottom layer in a stack of GEM foils will be patterned in order to read an X-Y position, with resolutions down to 10's of mm. The resolution can be improved by reconstructing the collected charge center of gravity in the X and Y directions.

According to other embodiments, other detector choices can be used such thin CCD films and/or pixel or strip-semiconductor detectors (e.g. Silicon, Diamond, CdZnTe, GaN, etc.). These may also be coupled to a GEM in order to improve detector signal or for read-out of the GEM itself. For surface detectors planar geometries are also possible, which simplifies detector choices.

Many of the described embodiments provide significant improvements over the prior art in subsurface density mapping and monitoring over large areas and volumes. Also described, according to some embodiments is a fiber-based or other finely segmented scintillator detector that is ideally suited to subsurface density measurements.

Whereas many alterations and modifications of the subject matter disclosed will no doubt become apparent to a person of ordinary skill in the art after having read the foregoing description, it is to be understood that the particular embodiments shown and described by way of illustration are in no way intended to be considered limiting. Further, the subject matter disclosed has been described with reference to particular embodiments, but variations within the spirit and scope of the subject matter disclosed will occur to those skilled in the art. It is noted that the foregoing examples have been provided merely for the purpose of explanation and are in no way to be construed as limiting of the subject matter disclosed. While the subject matter disclosed has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the subject matter disclosed in its aspects. Although the subject matter disclosed has been described herein with reference to particular means, materials and embodiments, the subject matter disclosed is not intended to be limited to the particulars disclosed herein; rather, the subject matter disclosed extends to all functionally equivalent structures, methods and uses, such as are within the scope of the appended claims.

What is claimed is:

1. A borehole system for making subterranean nuclear measurements, the system comprising:
   a plurality of elongated scintillator members, each elongated scintillator member generating optical signals in response to cosmic rays, wherein the plurality of elongated scintillator members form a bundle of helically wound fibers;
   a first optical detector unit optically coupled to each elongated scintillator member of the plurality of elongated scintillator members so as to detect optical signals from each elongated scintillator member; and
   a housing being suitable for subterranean deployment, wherein the housing houses the plurality of elongated scintillator members and the first optical detector.

2. The system according to claim 1, wherein the first optical detector unit optically coupled to a first end of each elongated scintillator member of the plurality of elongated scintillator members, and the system further comprises:
   a second optical detector unit optically coupled to a second end of each elongated scintillator member of the plurality of elongated scintillator members; and
   a processing system adapted and programmed to calculate impact position information, along one or more elongated scintillator members, for cosmic rays based at least in part on a comparison of optical signal arrival times at the first and second optical detector units.

3. The system according to claim 2, wherein the processing system is further adapted and programmed to calculate trajectory information for cosmic rays based at least in part on the calculated impact position information from at least two scintillator members.

4. The system according to claim 1, wherein each elongated scintillator member of the plurality of elongated scintillator members is selected from the group consisting of: a plastic scintillator fiber, an inorganic crystal fiber, a liquid-based scintillator in a long aspect ratio geometry, and a composite fiber.

5. The system according to claim 4, wherein each elongated scintillator member of the plurality of elongated scintillator members is selected from the group consisting of: a plurality of fibers with a rounded cross-section, a plurality of fibers with a polygonal cross-section, and a plurality of fibers with a varying cross-section.

6. The system according to claim 5, wherein each elongated scintillator member of the plurality of elongated scintillator members is selected from the group consisting of: a plurality of fibers with a hollow core, a plurality of photonic-crystal fibers, and microstructured fibers.

7. The system according to claim 4, wherein at least one elongated scintillator member of the plurality of elongated scintillator members is doped so as enhance its optical properties.

8. The system according to claim 4, wherein at least one elongated scintillator member of the plurality of elongated scintillator members is doped so as to better match the optical signals to the sensitivity of the first optical detector unit.

9. The system according to claim 1, wherein the plurality of elongated scintillator members are arranged around a hollow core volume which contains detector bias and data memory.

10. The system according to claim 1, wherein the plurality of elongated scintillator members are arranged around a hollow core volume through which a fluid flow channel is positioned.

11. The system according to claim 1, wherein the plurality of elongated scintillator members are arranged around a hollow core volume which contains a detector selected from the group consisting of: a Cerenkov detector and a transition radiation detector adapted to tag incoming ultra-relativistic cosmic ray muons.

12. The system according to claim 1, wherein the first optical detector unit includes at least one optical detector with at least one independent optical amplification channel and each elongated scintillator member of the plurality of elongated scintillator members is optically coupled to the at least one optical detector with a different optical amplification channel.

13. The system according to claim 12, wherein the at least one optical detector is a solid-state optical detector.

14. The system according to claim 13, wherein the at least one optical detector is selected from the group consisting of: a photo-diode or a solid-state photo-multiplier.

15. The system according to claim 12, wherein the at least one optical detector is an electron avalanche optical detector.

16. The system according to claim 15, wherein the at least one optical detector is of a type selected from the group consisting of: a photo-multiplier and a multi-channel plate.

17. The system according to claim 1, further comprising a data storage system housed within the housing adapted to store data generated by the first optical detector unit.

18. The system according to claim 1, further comprising:
   a battery system housed within the housing and adapted to supply power to the first optical detector unit for at least six months of operation.

19. The system according to claim 1, further comprising:
   a cable link from a surface of the earth adapted to supply power to the first optical detector unit for at least six months of operation.

20. The system according to claim 1, wherein the bundle of helically wound fibers includes multiple layers of fibers.

21. The system according to claim 20, wherein the multiple layers of fibers are wound in opposite directions.

22. A method for monitoring displacement of fluids within an area of interest within a subterranean formation, the method comprising:
   deploying a tool housing into a subterranean formation, the housing containing a plurality of elongated scintillator members, each elongated scintillator member generating optical signals in response to cosmic rays;
   detecting optical signals from one or more elongated scintillator members of the plurality of elongated scintillator members using a first optical detector unit that is optically coupled to each elongated scintillator member;

using the optical signals to identify cosmic rays that have traversed the area of interest within the subterranean formation; and using the identified cosmic rays to monitor displacement of fluids over time within the area of interest.

23. The method according to claim 22, further comprising:

detecting optical signals from one or more elongated scintillator members of the plurality of elongated scintillator members using the first optical detector unit that is optically coupled to a first end of each elongated scintillator member and a second optical detector unit that is optically coupled to a second end of each elongated scintillator member; and calculating impact position information, along the one or more elongated scintillator members, for cosmic rays based at least in part on a comparison of optical signal arrival times at the first and second optical detector units.

24. The method according to claim 23, further comprising;

calculating trajectory information for the cosmic rays based at least in part on the calculated impact position information and on information relating to which of the plurality of scintillator members generated optical signals.

25. The method according to claim 22, further comprising: injecting an injection fluid into the subterranean formation from one or more injection wells.

26. The method according to claim 25, wherein the injection of fluid is performed to store the injection fluid in an underground reservoir.

27. The method according to claim 25, wherein the injection fluid is steam and the steam is injected as part of a steam assisted gravity drainage operation.

28. The method according to claim 25, wherein the injection fluid is water and the injection of water is performed to stimulate a hydrocarbon reservoir.

29. The method according to claim 25, wherein the injection fluid is a gas and the injection of gas is performed to stimulate a hydrocarbon reservoir.

30. The method according to claim 22, wherein the housing further contains a battery system housed within the housing and adapted to supply power to the first optical detector unit for at least six months of operation.

31. The method according to claim 22, wherein the housing further contains a data storage system adapted to store data generated by the first optical detector unit.

* * * * *